United States Patent
Katsumoto et al.

(10) Patent No.: US 9,505,010 B2
(45) Date of Patent: Nov. 29, 2016

(54) FLOW CHANNEL DEVICE AND SORTING APPARATUS

(71) Applicant: Sony Corporation, Tokyo (JP)

(72) Inventors: Yoichi Katsumoto, Tokyo (JP); Kazumasa Sato, Tokyo (JP); Keiwa Sakai, Tokyo (JP)

(73) Assignee: SONY CORPORATION, Tokyo (JP)

( * ) Notice: Subject to any disclaimer, the term of this patent is extended or adjusted under 35 U.S.C. 154(b) by 112 days.

(21) Appl. No.: 14/189,261

(22) Filed: Feb. 25, 2014

(65) Prior Publication Data

US 2014/0246322 A1    Sep. 4, 2014

(30) Foreign Application Priority Data

Mar. 4, 2013  (JP) ................. 2013-041900

(51) Int. Cl.
    *B03C 5/00*     (2006.01)
    *G01N 15/10*     (2006.01)
    *B03C 5/02*     (2006.01)

(52) U.S. Cl.
    CPC ............. *B03C 5/005* (2013.01); *B03C 5/026* (2013.01); *G01N 15/1031* (2013.01); *G01N 2015/1081* (2013.01)

(58) Field of Classification Search
    CPC ......... B03C 5/005; B03C 5/026; B03C 5/00; B01L 2400/0424; G01N 27/221; G01N 27/447; B01D 57/02

See application file for complete search history.

(56) References Cited

U.S. PATENT DOCUMENTS

| | | | |
|---|---|---|---|
| 2006/0177815 A1* | 8/2006 | Soh ................... | B01L 3/502761 435/4 |
| 2007/0125941 A1* | 6/2007 | Lee ................... | B01L 3/502761 250/251 |
| 2010/0006441 A1* | 1/2010 | Renaud ............. | B01L 3/502746 204/643 |
| 2012/0103817 A1* | 5/2012 | Omori ............... | B01L 3/502761 204/643 |

FOREIGN PATENT DOCUMENTS

JP      2012-098075      5/2012

* cited by examiner

*Primary Examiner* — Gurpreet Kaur
(74) *Attorney, Agent, or Firm* — Chip Law Group

(57) ABSTRACT

Provided is a flow channel device including: a flow channel through which a fluid including particles flow; a plurality of branch channels branching from the flow channel; a measurement portion that is provided at a predetermined position in the flow channel and configured to measure electrical characteristics when the particles pass the predetermined position; an operation portion that is provided on a downstream side of the measurement portion and on an upstream side of the plurality of branch channels and configured to apply a dielectrophoretic force to the particles by forming an electric field; and an electrical first guard portion provided between the measurement portion and the operation portion.

9 Claims, 9 Drawing Sheets

FLOW CHANNEL DEVICE AND SORTING APPARATUS

CROSS REFERENCE TO RELATED APPLICATIONS

This application claims the benefit of Japanese Priority Patent Application JP 2013-041900 filed Mar. 4, 2013, the entire contents of which are incorporated herein by reference.

BACKGROUND

The present disclosure relates to a flow channel device that causes particles of cells and the like to flow and a sorting apparatus including the flow channel device.

From the past, as one of various systems of cell sorters (cell sorting apparatuses), there is a system that sorts cells using a dielectrophoretic method.

Japanese Patent Application Laid-open No. 2012-98075 (hereinafter, referred to as Patent Document 1) discloses a cell sorting apparatus (cell analysis/sorting system) that uses the dielectrophoretic method.

The cell sorting apparatus includes a cell sorting chip that includes a micro flow channel. This apparatus measures, when a fluid including cells flows through predetermined flow channels in the chip, a complex impedance and a complex permittivity among the flow channels and sorts the cells based on the measurement result. The chip includes a signal detection electrode (measurement portion) for measuring a complex impedance and a complex permittivity of cells and detecting signals.

The chip also includes as a cell sorting means, on a downstream side of the signal detection electrode, an operation electrode (electric field application portion) having a predetermined shape, that is provided for forming an electric field for imparting an appropriate dielectrophoretic force to the cells. According to a difference in the state of the dielectrophoretic force via the operation electrode, that is, a difference in the electric field generation state, one of two branch channels provided downstream from the operation electrode is selected so as to cause the cells to flow through (see, for example, paragraphs (0025), (0028), etc. in specification of Patent Document 1).

SUMMARY

For generating a dielectrophoretic force effective for particles, there is a need to apply a relatively-large voltage to the operation electrode. Therefore, noises may be caused in measurement values obtained by a measurement electrode due to the applied voltage to the operation electrode. As a result, since measurement accuracy is lowered, there is a fear that sorting accuracy may be lowered.

In view of the circumstances as described above, there is a need for a flow channel device and a sorting apparatus that are capable of reducing noises in measurement values obtained by the measurement portion and improving measurement accuracy.

According to an embodiment of the present disclosure, there is provided a flow channel device including a flow channel, a plurality of branch channels, a measurement portion, an operation portion, and an electrical first guard portion.

Through the flow channel, a fluid including particles flow.

The plurality of branch channels branch from the flow channel.

The measurement portion is provided at a predetermined position in the flow channel and configured to measure electrical characteristics when the particles pass the predetermined position.

The operation portion is provided on a downstream side of the measurement portion and on an upstream side of the plurality of branch channels and configured to apply a dielectrophoretic force to the particles by forming an electric field.

The first guard portion is provided between the measurement portion and the operation portion.

By providing the electrical guard portion between the measurement portion and the operation portion, a current generated by the operation portion is captured by the guard portion. As a result, noises in measurement values obtained by the measurement portion are reduced, and measurement accuracy is improved.

The operation portion receives an operation signal generated based on a signal obtained by the measurement portion and forms an electric field corresponding to the operation signal.

The first guard portion may include a guard electrode facing an inside of the flow channel.

The guard electrode may be provided on at least one of two opposing sides of the flow channel.

The guard electrode may include a common potential. With this structure, an effect of capturing charges from the operation portion is promoted.

The flow channel device may further include an electrical second guard portion provided in the measurement portion. With this structure, by providing the second guard portion in the measurement portion in addition to the first guard portion, noises in the measurement values obtained by the measurement portion are additionally reduced.

The measurement portion may include a measurement electrode pair, and the second guard portion may include a guard electrode pair intersecting the measurement electrode pair.

The flow channel device may be structured by laminating a plurality of resin films. In addition, the guard electrode may be formed of at least one of the plurality of resin films. With this structure, the guard electrode can be formed in the film in advance when producing the flow channel device, and thus productions of the guard electrode and the flow channel device become easy.

At least two of the plurality of resin films may be formed of the same material. In addition, the guard electrode may be a guard electrode pair opposing the two resin films. Since at least two resin films are formed of the same material and the guard electrode pair is formed in the resin films, this structure is suited for a mass production of resin films and can improve productivity of the flow channel device.

According to another embodiment of the present disclosure, there is provided a sorting apparatus including the flow channel device and a controller The controller is electrically connected to the measurement portion and the operation portion and configured to generate an operation signal based on a signal obtained by the measurement portion and output the operation signal.

As described above, according to the embodiments of the present disclosure, it is possible to reduce noises in measurement values obtained by the measurement portion and improve measurement accuracy.

These and other objects, features and advantages of the present disclosure will become more apparent in light of the following detailed description of best mode embodiments thereof, as illustrated in the accompanying drawings.

DETAILED DESCRIPTION OF EMBODIMENTS

Hereinafter, embodiments of the present disclosure will be described with reference to the drawings.

[First Embodiment]

(Structure of Sorting Apparatus)

Figure 1:
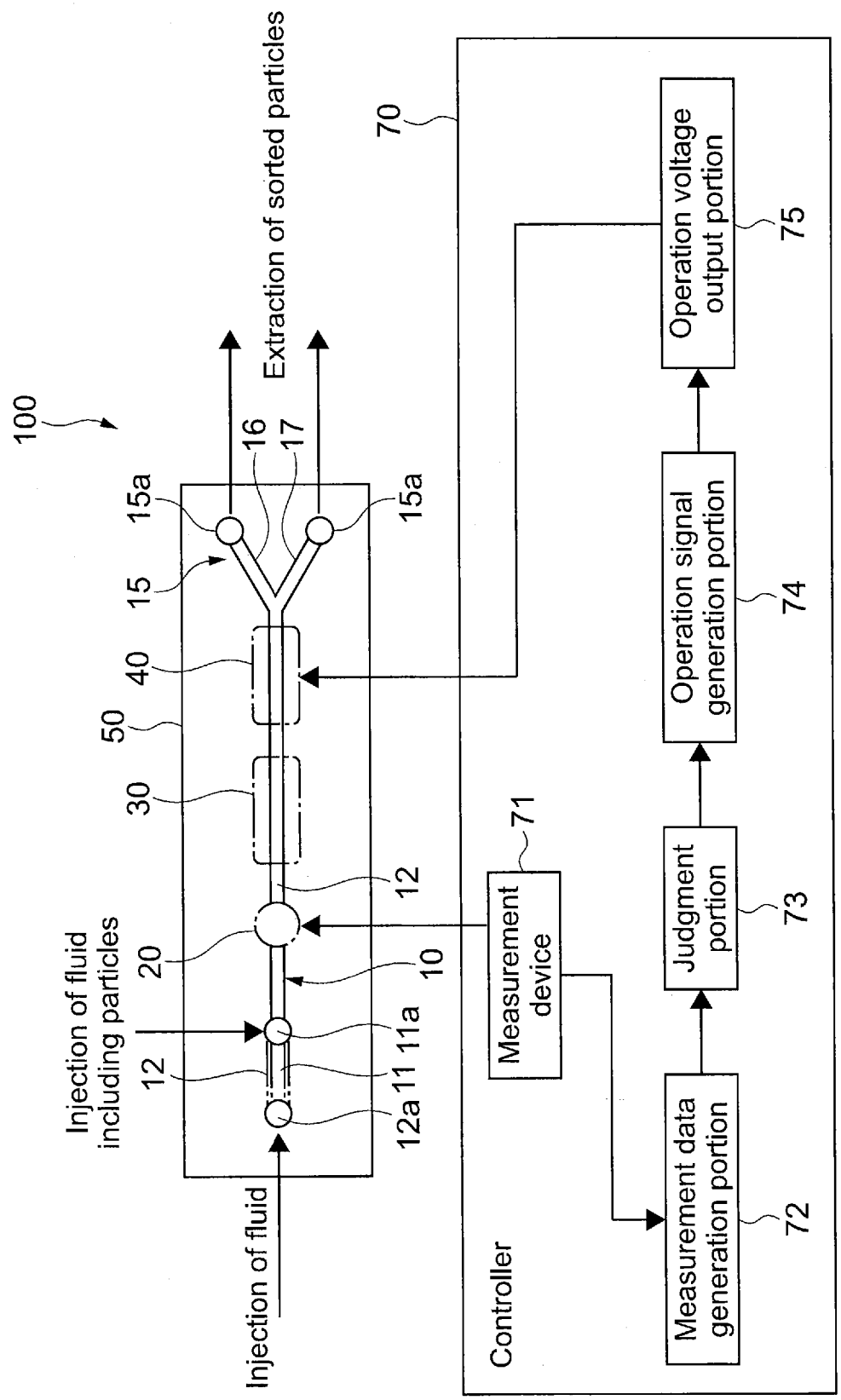
FIG. 1 is a block diagram showing a structure of a sorting apparatus according to a first embodiment of the present disclosure.

FIG. 1 is a block diagram showing a structure of a sorting apparatus according to a first embodiment of the present disclosure. The sorting apparatus 100 includes a flow channel device 50 and a controller 70.

The flow channel device 50 is formed in, for example, a chip shape and includes a flow channel 10. Through the flow channel 10, a fluid including particles as a sample flows. The flow channel 10 is a micro flow channel having a small width of about 30 to 200 µm, for example.

The flow channel device 50 includes, from an upstream side on the left-hand side of the figure, a measurement portion 20, a guard portion 30 (first guard portion), an operation portion 40, and a branch portion 15 along the flow channel 10.

The particles as a sample are, for example, biological cells, that is, leucocytes and erythrocytes. When the particles are cells, a normal saline solution or the like is selected as the fluid.

Figure 2:
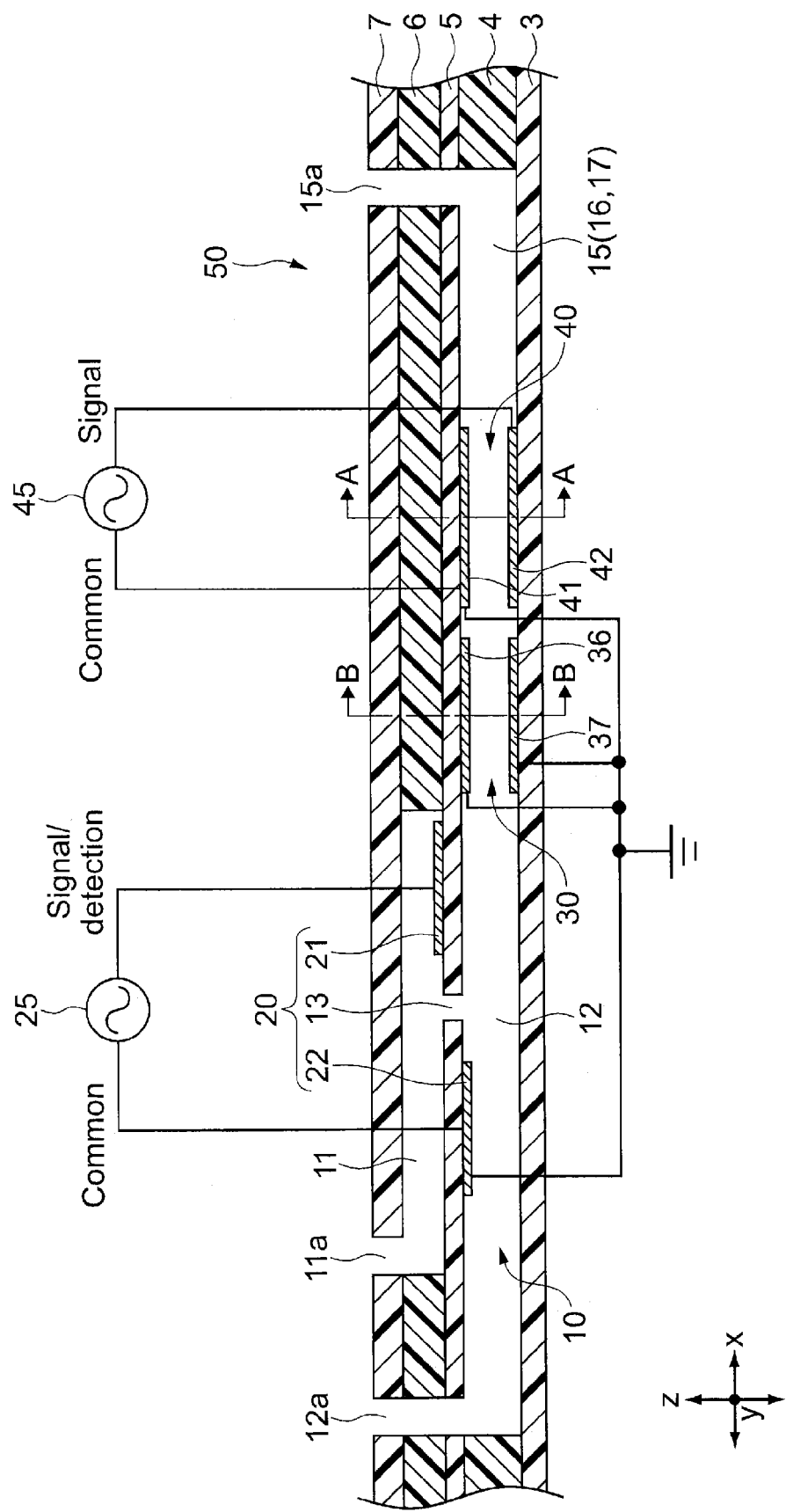
FIG. 2 is a schematic cross-sectional diagram of a flow channel device taken along a direction of a flow channel.

FIG. 2 is a schematic cross-sectional diagram of the flow channel device 50 taken along a direction of the flow channel 10. The flow channel device 50 includes the 2-stage flow channel 10 in a thickness direction of the flow channel device 50. In FIG. 2, a first flow channel 11 provided on an upstream side includes a first inlet 11a, and a fluid including particles is caused to flow through the first flow channel 11 via the first inlet 11a using a pipette, a pump, and the like (not shown). Since the particles are aligned along a flowing direction in the first flow channel 11, it is favorable to cause the fluid to flow through the first inlet 11a at a constant flow rate using a syringe pump or the like.

A second flow channel 12 provided on a downstream side includes a second inlet 12a, and a fluid not including particles is caused to flow through the second flow channel 12 via the second inlet 12a using a pump or other apparatuses (not shown). It is favorable for the pressure of the fluid that flows into the second flow channel 12 via the second inlet 12a to be constant.

Figure 3:
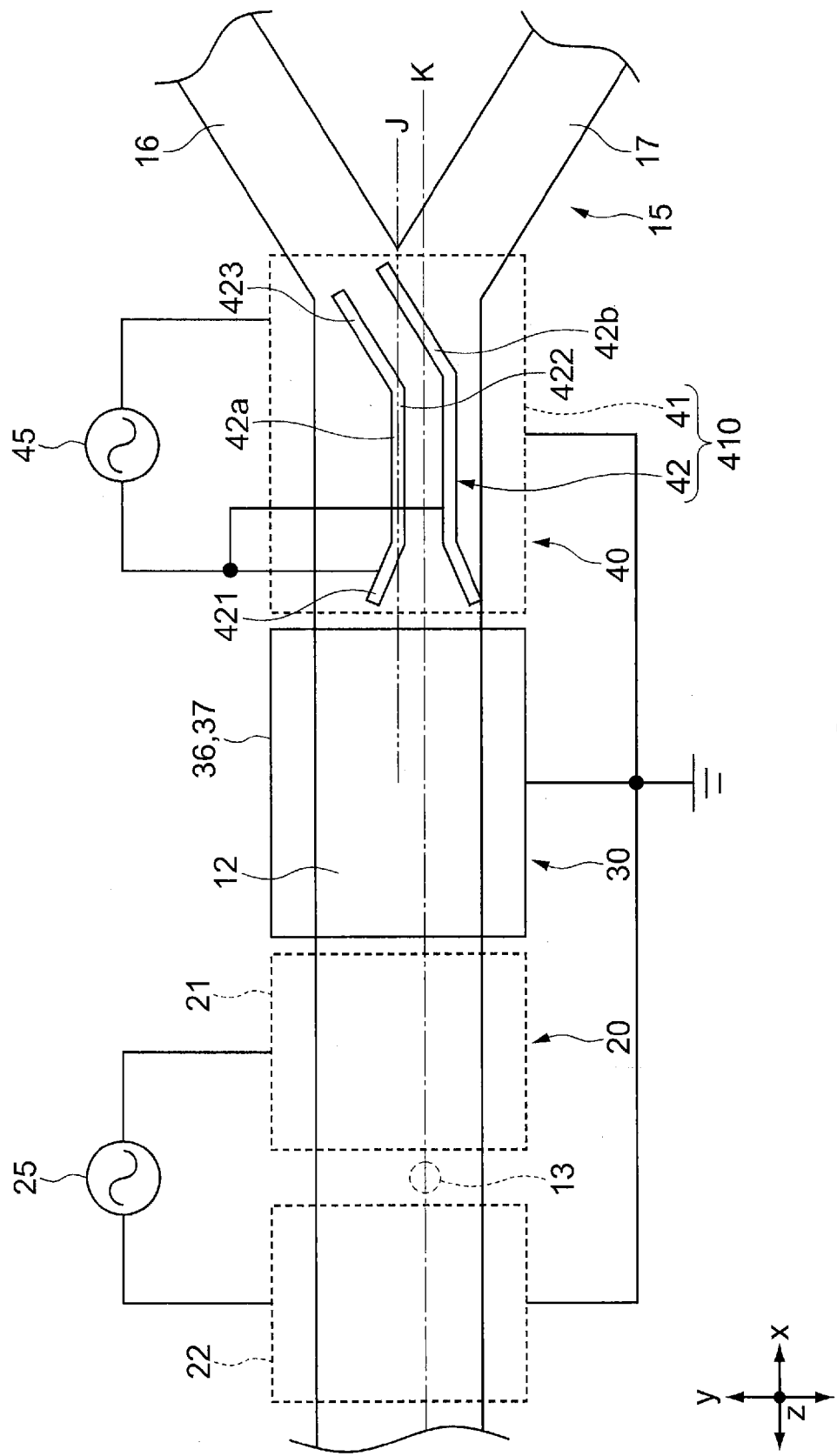
FIG. 3 is a plan view of a second flow channel and a branch portion branching from the second flow channel.

FIG. 3 is a plan view of the second flow channel 12 and the branch portion 15 branching from the second flow channel 12. The second flow channel 12 is formed practically in a Y shape. The portion formed in the Y shape is the branch portion 15, which includes a plurality of (e.g., two) branch channels 16 and 17. At downstream end portions of the branch channels 16 and 17, outlets 16a and 17a are provided as shown in FIG. 1. It should be noted that a pool (not shown) for pooling sorted particles may be provided on the upstream side of the outlets 16a and 17a.

As shown in FIGS. 2 and 3, the first flow channel 11 and the second flow channel 12 are in communication with each other via a narrowed channel 13. As shown in FIG. 3, the narrowed channel 13 is provided on, for example, a line K in FIG. 3 at a position deviated from a center of the second flow channel 12 (position of branch reference line J) in a y direction as a width direction. On an extension of the line K toward the downstream side, a guide electrode portion 42 of the operation portion 40 is provided as will be described later.

As described above, by splitting the flow channel 10 into the first flow channel 11 and the second flow channel 12, an alignment of the particles can be promoted by a constant flow rate in the first flow channel 11 and the narrowed channel 13, and a pressure gradient of the fluid in the second flow channel 12 can be determined dominantly in the second flow channel 12. Accordingly, since a stability of a fluid pressure at an outlet portion of the narrowed channel 13 can be enhanced, a flow rate of the fluid that passes the narrowed channel 13 can be stabilized.

It should be noted that the terms "up" and "down" are irrelevant to the gravity direction. In the specification, the terms "up" and "down" are used for convenience.

In FIG. 1, the first flow channel 11 on the upstream side and the second flow channel 12 on the downstream side are parallel in the x direction and overlap each other in a plan view. However, the structure is not limited to such a structure, and the direction of the flow channels 10 does not need to be parallel and/or the flow channels do not need to overlap each other in a plan view. In other words, as long as the first flow channel 11 and the second flow channel 12 are connected via the narrowed channel 13, the flow channels 10 may be formed in any direction. In this case, a drainage channel or a drainage outlet may be connected to only the first flow channel 11.

As shown in FIGS. 2 and 3, the narrowed channel 13 described above is provided at a predetermined position between the first flow channel 11 and the second flow channel 12. The narrowed channel 13 has a flow channel size enough for a single particle to flow through, for example, and the particles that flow through the first flow channel 11 flow into the second flow channel 12 via the narrowed channel 13.

As shown in FIGS. 2 and 3, the measurement portion 20 includes an area of the narrowed channel 13. Specifically, the measurement portion 20 includes measurement electrodes 21 and 22 sandwiching the narrowed channel 13. The measurement electrodes 21 and 22 are electrodes for measuring electrical characteristics when the particles pass through the narrowed channel 13. The measurement electrodes 21 and 22 are provided on upper and lower surfaces of a center resin film 5 out of resin films 3 to 7 laminated as shown in FIG. 2, for example, and constitute a parallel plate capacitor. An AC power supply 25 is connected to the measurement electrodes 21 and 22 so that a predetermined AC voltage of an mV order can be applied. The measurement electrode 22 is a common electrode.

Figure 4:
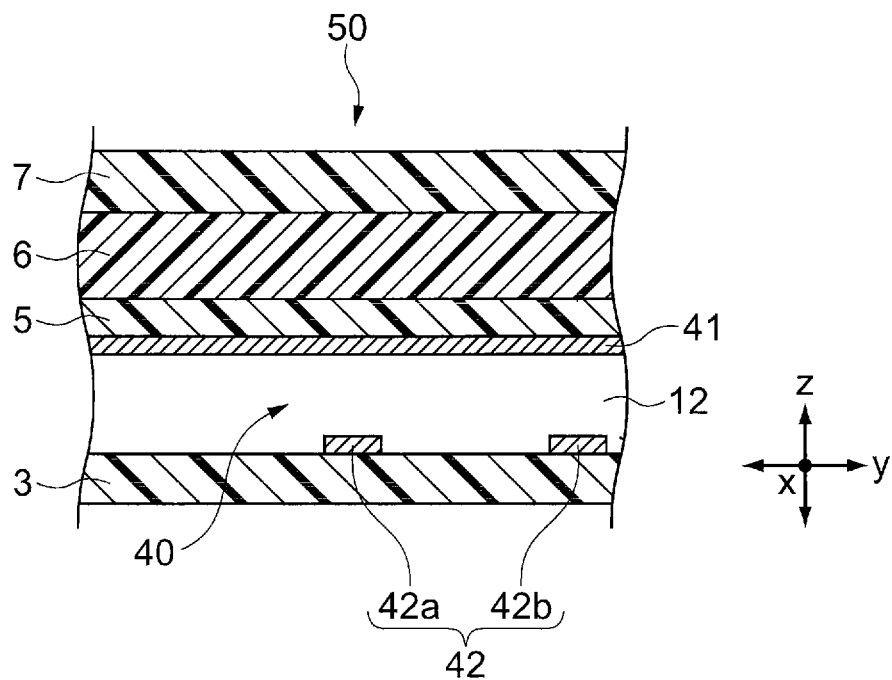
FIG. 4 is a cross-sectional diagram taken along the line A-A of FIG. 2.

The operation portion 40 is provided on the upstream side of the branch portion 15, specifically, right before the branch portion 15, and forms a guide electric field having a predetermined electric field intensity gradient so as to apply a dielectrophoretic force to the particles flowing through the flow channel 10. The operation portion 40 includes an operation electrode 410 therefor. FIG. 4 is a cross-sectional diagram taken along the line A-A of FIG. 2.

As shown in FIGS. 3 and 4, the operation electrode 410 includes a common electrode 41 provided at an upper portion of the second flow channel 12 and a guide electrode portion 42 provided on a lower portion thereof.

An AC power supply 45 is connected to the operation electrode 410, and an AC operation voltage is applied between the common electrode 41 and the guide electrode portion 42. The common electrode 41 functions as a ground electrode and is maintained at a ground potential (common potential).

The guide electrode portion 42 typically includes a plurality of (e.g., two) elongated line electrodes 42a and 42b. For example, the branch portion 15 is branched into the branch channels 16 and 17 at a position on the branch reference line J set at substantially the center of the second flow channel 12 in the width direction (y direction). The guide electrode portion 42 is provided at a position deviated from the branch reference line J in the y direction so that the line K described above is positioned between the line electrodes 42a and 42b. Accordingly, particles that has flown into the second flow channel 12 via the narrowed channel 13 flow along the x direction as they are with the fluid to be introduced into the line electrodes 42a and 42b.

The guide electrode portion 42 includes an introduction portion 421, a straight portion 422, and a direction change portion 423. The introduction portion 421 is formed such that the line electrodes 42a and 42b approach each other from the upstream side to the downstream side. The straight portion 422 is formed along the second flow channel 12, that is, formed to be parallel to the x direction. The direction change portion 423 is formed such that the direction is changed from the straight portion 422 so as to be directed toward the branch channel 16 as one of the branch channels. A voltage is applied to the line electrodes 42a and 42b so that the line electrodes 42a and 42b have the same potential.

As an AC operation voltage is applied to the operation electrode 410, a guide electric field is formed between the common electrode 41 and the guide electrode portion 42. The guide electric field imparts a dielectrophoretic force such that the particles travel between the line electrodes 42a and 42b. For example, an amplitude of the AC voltage applied to the operation electrode 410 is 1 V to 30 V, and a frequency thereof is 1 kHz to 100 kHz. Accordingly, the channel of the particles can be changed between a time a voltage is applied to the operation electrode 410 and a time a voltage is not applied, and the particles can be selectively caused to flow into either the branch channel 16 or 17.

As described above, the guide electric field as follows is basically formed by the guide electrode portion 42 (two line electrodes 42a and 42b) and one common electrode 41 opposing it. In other words, an electric field intensity gradient in the z direction is caused between the guide electrode portion 42 and the common electrode 41, and an electric field intensity gradient in the y direction is caused between the two line electrodes 42a and 42b.

The dielectrophoretic force is controlled by the electric field intensity gradient, that is, a density change of an electric force line. This point differs from an electrophoretic force that is generated in a direction along the electric force line. In other words, the dielectrophoretic force is not always generated in the direction along the electric force line. In this embodiment, since the two line electrodes 42a and 42b have substantially the same potential, the line electrodes 42a and 42b generate an electric field intensity gradient directed toward the center thereof (position of line K), that is, an electric field intensity gradient in the y direction. In this embodiment, it has been confirmed that the electric field intensity gradient in the y direction is more precipitous than that in the z direction. Therefore, although a dielectrophoretic force in the z direction is once applied to the particles that have flown between the line electrodes 42a and 42b, the particles gradually approach the guide electrode portion 42 (away from common electrode 41) and are settled at a position on the line K at the center of the line electrodes 42a and 42b. Consequently, also in the direction change portion 423, the particles settle between the line electrodes 42a and 42b by the precipitous electric field intensity gradient in the y direction. In other words, since the particles move along the line electrodes 42a and 42b, a movement direction thereof can be changed.

It should be noted that the applicant of the present disclosure specifically discloses in another application a simulation of generating a dielectrophoretic force by the guide electric field.

Figure 5:
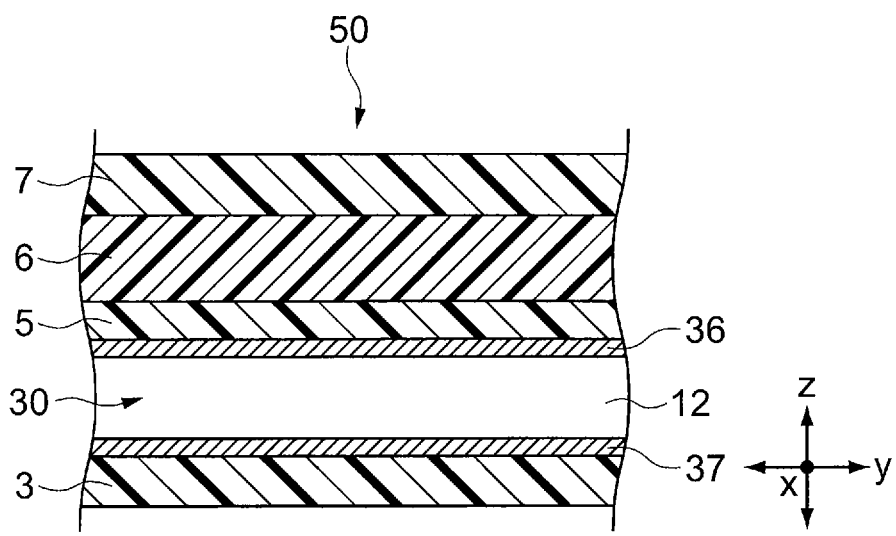
FIG. 5 is a cross-sectional diagram taken along the line B-B of FIG. 2.

FIG. 5 is a cross-sectional diagram taken along the line B-B of FIG. 2 showing the guard portion 30. The guard portion 30 includes a plurality of (e.g., two) guard electrodes 36 and 37 facing an inside of the second flow channel 12. Specifically, the guard electrodes 36 and 37 are provided substantially in parallel with each other while opposing each other on an upper portion side and lower portion side of the second flow channel 12 and constitute an electrode pair. The guard electrodes 36 and 37 are grounded. The size, area, shape, and the like of the guard electrodes 36 and 37 are substantially the same but may also differ. Since the guard portion 30 is positioned between the measurement portion 20 and the operation portion 40, the guard portion 30 exerts an electrical guard function between them. Specifically, the guard portion 30 is capable of suppressing noise incorporations in the measurement portion 20 due to voltage signals applied to the operation portion 40.

As shown in FIG. 1, the controller 70 is electrically connected to the measurement portion 20 and the operation portion 40, generates an operation signal based on a measurement signal obtained by the measurement portion 20, and outputs an operation voltage corresponding to the signal to the operation portion 40. Specifically, the controller 70 includes a measurement device 71, a measurement data generation portion 72, a judgment portion 73, an operation signal generation portion 74, and an operation voltage output portion 75. The controller 70 is typically constituted of a computer.

The measurement device 71 applies an AC voltage of an arbitrary frequency within a predetermined frequency range to the measurement electrodes 21 and 22. When the particles pass the narrowed channel 13, a resistance value between the measurement electrodes 21 and 22 changes. The measurement device 71 detects a current flowing between the measurement electrodes 21 and 22. The measurement data generation portion 72 calculates a complex impedance from the current value. Specifically, the measurement data generation portion 72 calculates, with respect to individual cells flowing through the narrowed channel 13, across multipoint frequencies (3 points or more, typically about 10 to 20 points or more) within an AC voltage frequency range (e.g., 0.1 MHz to 50 MHz) at which a dielectric relaxation phenomenon occurs, a complex permittivity that depends on those cells.

It should be noted that in actuality, the measurement data generation portion 72 calculates a complex permittivity by a known electric conversion expression based on the complex impedance calculated as described above, and obtains data including the complex permittivity as measurement data.

As an amount electrically equivalent to the complex permittivity, there are a complex impedance, a complex admittance, a complex capacitance, a complex conductance, and the like, those of which can be mutually converted by the simple known electric amount conversion described above. Moreover, the measurement of a complex impedance or a complex permittivity includes a measurement of only a real part or imaginary part.

The judgment portion 73 acquires the measurement data output from the measurement data generation portion 72 and judges whether the particles are to be sorted based on the measurement data, that is, whether the particles are to be guided to a predetermined one of the branch channels (branch channel 16 in this embodiment) of the branch portion 15. Specifically, the judgment portion 73 carries out the judgment processing by collating a judgment condition of data on a complex permittivity that has been arbitrarily set in advance in a memory for sorting desired particles with the measurement data.

The operation signal generation portion 74 generates an operation signal when the measurement target particles are to be sorted (here, particles to be guided to branch channel 16), and does not generate an operation signal otherwise. It is also possible for the operation signal generation portion 74 to not generate an operation signal when the measurement target particles are to be sorted and generate an operation signal otherwise.

The operation voltage output portion 75 outputs the AC operation voltage based on the operation signal obtained from the operation signal generation portion 74.

(Method of Producing Flow Channel Device)

As a production method for the flow channel device 50 of this embodiment, there is a method as follows.

For example, a plurality of resin films (insulator films), for example, 5 resin films 3, 4, 5, 6, and 7 (see FIG. 2) are prepared. The electrodes including the measurement electrodes 21 and 22, the operation electrode 410, and the guard electrodes 36 and 37 are formed on, for example, 2 of the 5 resin films 3 to 7. Further, for forming the flow channel 10, the branch channels 16 and 17, the narrowed channel 13, and the inlets and outlets on the resin films, for example, grooves and holes are formed at predetermined positions as necessary. The electrodes, grooves, holes, and the like may be formed by photolithography and photo-etching, or may be formed by laser processing. The 5 resin films 3 to 7 on which the electrodes, grooves, and holes have been formed are positioned, laminated, and subjected to heat pressure bonding, with the result that the flow channel device 50 as shown in FIG. 2 is formed.

It is favorable for two or more of the plurality of resin films to be formed of the same material. In this embodiment, the resin films 3, 5, and 7 are formed of the same material, and the resin films 4 and 6 are formed of the same material (material different from that of resin films 3, 5, and 7). In this case, the guard electrodes 36 and 37 become an opposing guard electrode pair provided on the resin films 3 and 5. As described above, since two or more resin films are formed of the same material and the guard electrodes 36 and 37 are formed on those resin films, this structure is suited for a mass production of the resin films, and thus a productivity of the flow channel device 50 can be improved.

As described above, in producing the flow channel device 50, the guard electrodes 36 and 37 and other electrodes can be formed on the resin films in advance before laminating the resin films 3 to 7, with the result that productions of the guard electrodes 36 and 37 and the flow channel device 50 become easy.

The guard electrodes 36 and 37 may be formed of, for example, copper, silver, gold, platinum, nickel, zinc, titanium, or stainless steel, or may be formed by carrying out various types of plating processing on them.

Further, as the materials for the measurement electrodes 21 and 22 and the operation electrode 410, the same material as the guard electrodes 36 and 37 can be used.

As the materials for the resin films 3 to 7, a polyimide film, a thermoplastic polyimide film, PDMS (polydimethylsiloxane or dimethylpolysiloxane), acryl, PES (polyethersulfone), polycarbonate, polypropylene, polystyrene, polyimide, COP (cyclic olefin polymer), COC (cyclic olefin copolymer), and the like are used. In this embodiment, one of the materials above is selected as the common material for forming the resin films 3, 5, and 7, and a material different from that of the resin films 3, 5, and 7 is selected as the common material for forming the resin films 4 and 6.

(Operation of Sorting Apparatus)

A fluid including particles flows into the first flow channel 11 via the first inlet 11a and flows through the first flow channel 11. On the other hand, a fluid not including particles flows through the second flow channel 12. The particles that flow through the first flow channel 11 join the flow of the second flow channel 12 via the narrowed channel 13.

A predetermined AC voltage is applied to the measurement electrodes 21 and 22 while the sorting apparatus 100 is being operated, and the measurement data generation portion 72 calculates a complex permittivity as described above and outputs it as measurement data when the particles pass the narrowed channel 13. As described above, the judgment portion 73 judges whether the particles are to be guided to the branch channel 16 based on the acquired measurement data.

Figure 6:
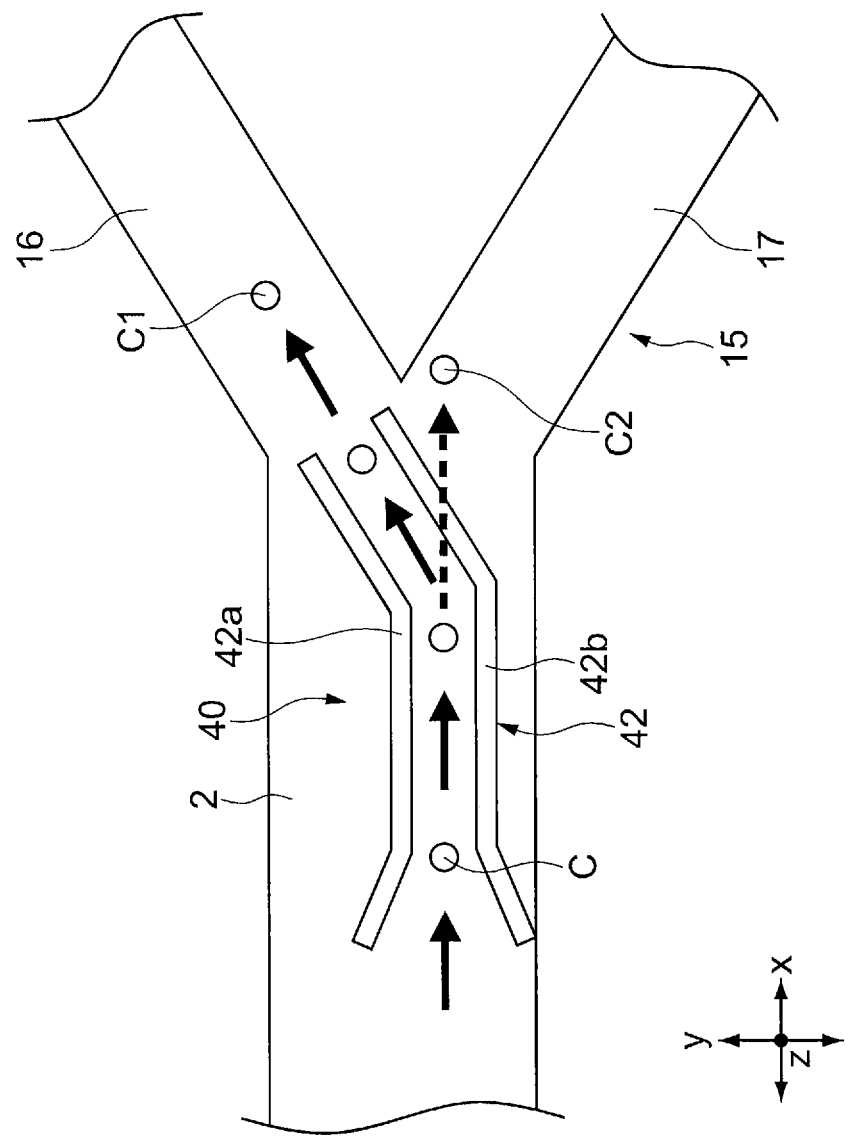
FIG. 6 shows a traveling direction of particles when an operation voltage is applied to a guide electrode portion and when the operation voltage is not applied to the guide electrode portion.

When judged that the particles are to be guided to the branch channel 16, the operation signal generation portion 74 generates a predetermined operation voltage and applies the operation voltage to the operation electrode 410 right before the particles flowing through the second flow channel 12 reach the guide electrode portion 42. As a result, as shown in FIG. 6, a guide electric field is formed in the operation portion 40, and particles C move along the line electrodes 42a and 42b by a dielectrophoretic force corresponding to the guide electric field to flow into the branch channel 16 as indicated by the symbol C1.

It should be noted that since the speed of the fluid including particles and the distance between the narrowed channel 13 and the operation portion 40 are determined in advance, the controller 70 can detect a timing right before the particles reach the guide electrode portion 42.

When judged that the particles are to be guided to the branch channel 17, the operation signal generation portion 74 does not generate an operation voltage. Therefore, a dielectrophoretic force caused by a guide electric field is not generated, and the particles move in the x direction as they are above the guide electrode portion 42 to pass and flow into the branch channel 17 as indicated by the symbol C2.

By the operation of the sorting apparatus 100 as described above, it is possible to distinguish normal cells and dead cells from each other or normal cells and cancer cells from each other, for example.

Here, the voltage applied to the operation electrode 410 in the operation portion 40 is 1 V to 30 V, and the voltage applied to the measurement electrodes 21 and 22 in the measurement portion 20 is of a mV order. In addition, the fluid is a conductive fluid and causes an electrical bonding. Therefore, when no countermeasure is taken, charges are generated from the operation portion 40 mainly as an ion current and flow into the measurement portion 20, with the result that measurement values of the measurement portion 20 are adversely affected. In this embodiment, however, since the electrical guard portion 30 is provided, the charges are captured by the guard portion 30. As a result, noises in the measurement values of the measurement portion 20 are reduced, and measurement accuracy is improved.

Moreover, when no countermeasure is taken in a case where an operation voltage application timing is indefinite, operation voltage signals are irregularly output to the measurement portion 20, and thus measurement accuracy is impaired. However, this can be prevented by the guard portion 30, and a stable measurement can be performed in the measurement portion 20 irrespective of the timing, with the result that an elaborate sorting becomes possible. Furthermore, even when the operation voltage amplitude is changed depending on the particle size, the adverse effect on the measurement portion 20 can be suppressed.

Figure 7:
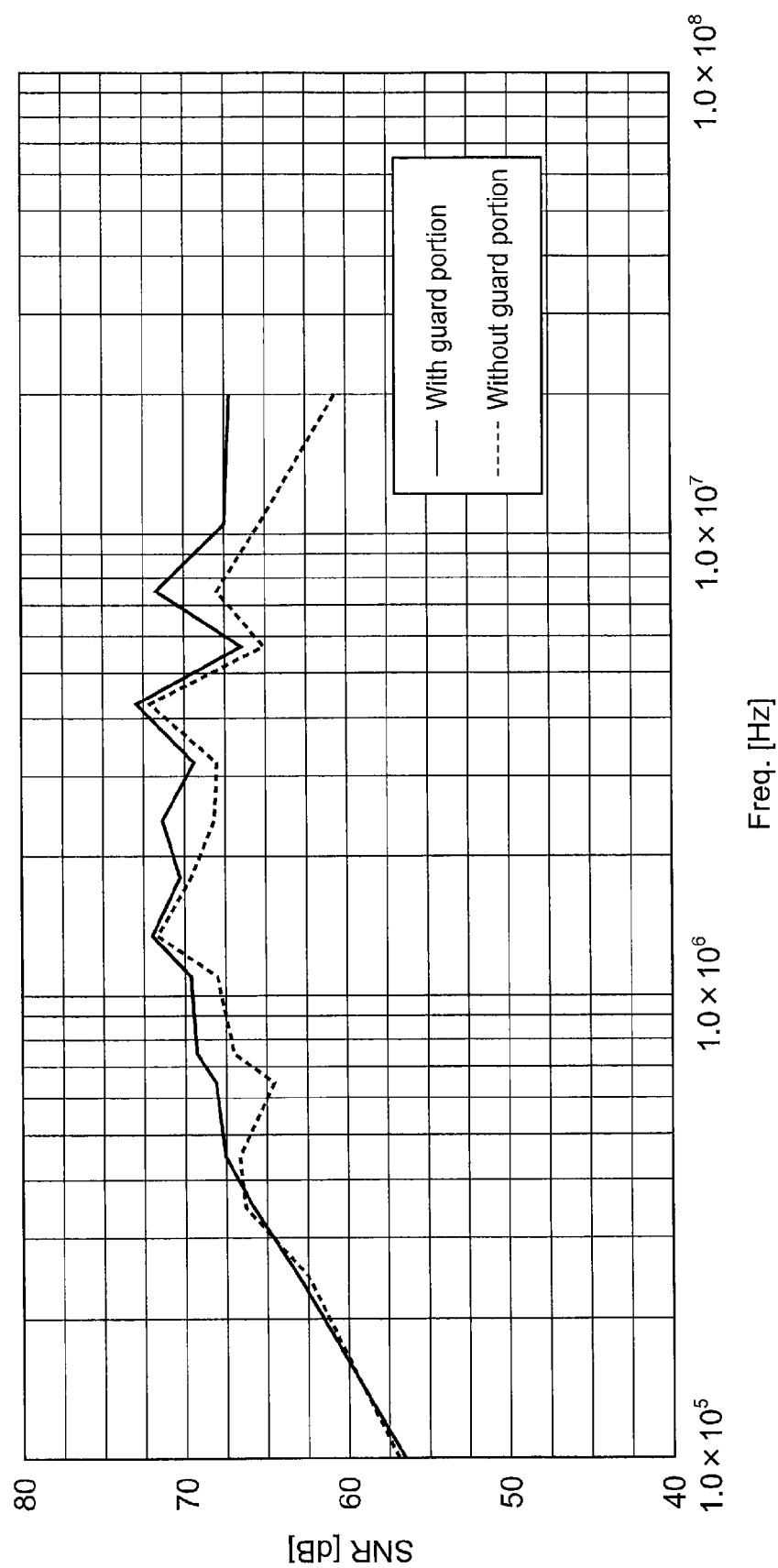
FIG. 7 shows measurement results of an SN ratio of a capacitance obtained by a measurement portion in a flow channel in which a guard portion is provided and a flow channel in which a guard portion is not provided.
Figure 8:
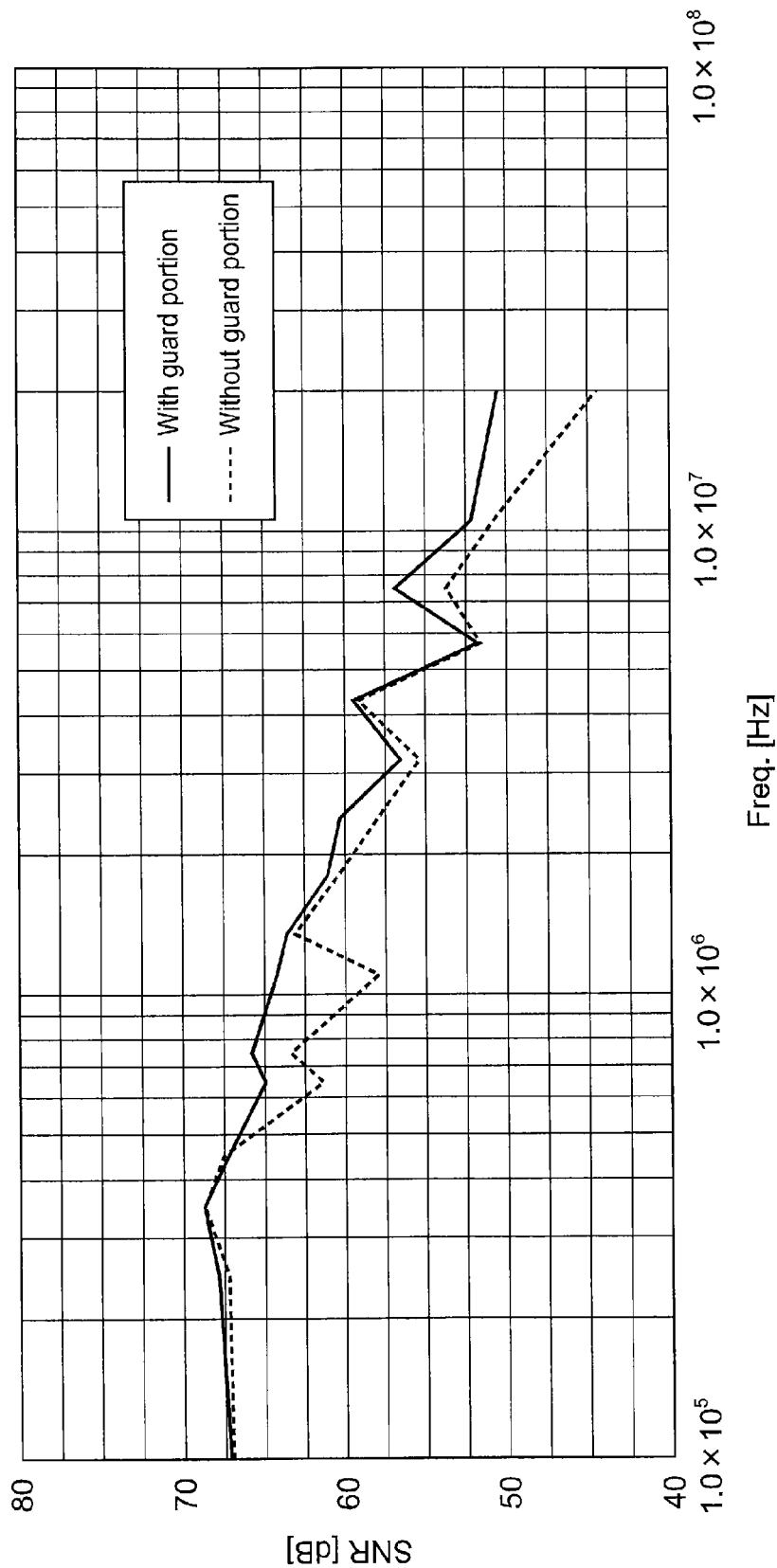
FIG. 8 shows measurement results of an SN ratio of a conductance obtained by the measurement portion in the flow channel in which a guard portion is provided and the flow channel in which a guard portion is not provided.

FIG. 7 shows measurement results of an SN ratio of a capacitance obtained by the measurement portion 20 in a flow channel in which the guard portion 30 is provided and a flow channel in which the guard portion 30 is not provided. FIG. 8 shows measurement results of an SN ratio of a conductance in the flow channel in which the guard portion 30 is provided and the flow channel in which the guard portion 30 is not provided. The abscissa axis represents a frequency.

As a measurement condition, an equivalent circuit constituted of a parallel circuit of a capacitance and a conductance is provided between the measurement electrodes 21 and 22. Other measurement conditions are as follows.

Fluid: Normal saline solution

Size of flow channel 10: Width of 200 μm (y-direction size), height of 50 μm (z-direction size)

Guard portion 30: Parallel plate electrode 2 mm in direction along flow of fluid (x direction)

Operation voltage: 20 Vp-p

Operation voltage frequency: 10 MHz

It can be seen that the SN ratio in the wide frequency area of 400 kHz or more is improved more in the device in which the guard portion 30 is not provided than the device in which the guard portion 30 is provided. In the frequency area smaller than 400 kHz, the effect of the operation voltage does not appear even when the guard portion 30 is not provided.

When living cells are used as the particles, a β relaxation in which features appear in the cells (relaxation particularly unique to a cell membrane out of dielectric relaxations) is present between 100 kHz and 30 MHz in general, so it can be seen that the effect is obtained in the necessary band.

[Second Embodiment]

Figure 9:
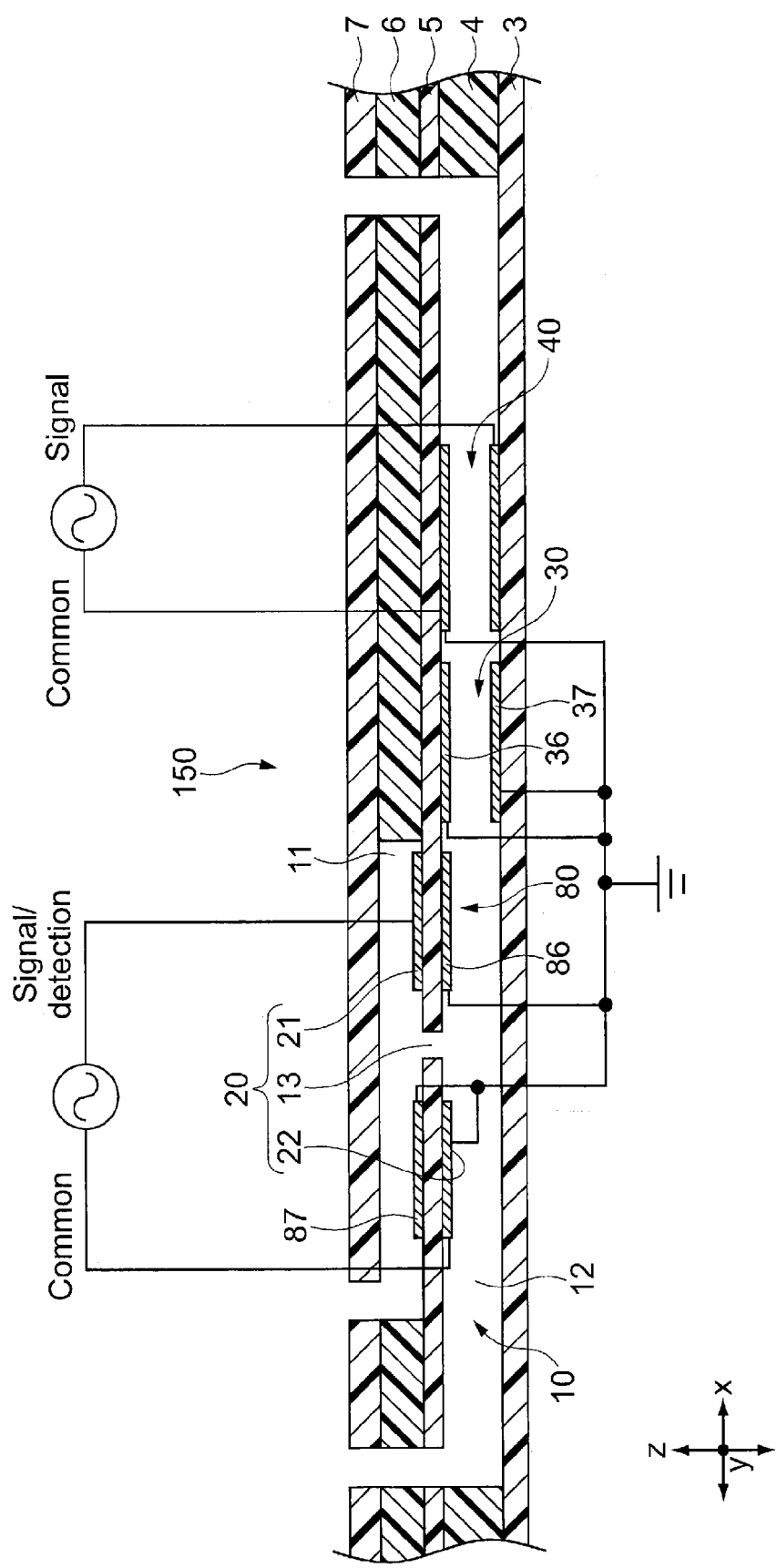
FIG. 9 is a cross-sectional diagram taken along a flow channel of a flow channel device according to a second embodiment of the present disclosure.

FIG. 9 is a cross-sectional diagram taken along a flow channel 10 of a flow channel device according to a second embodiment of the present disclosure. In descriptions below, descriptions on members, functions, and the like that are the same as those of the sorting apparatus 100 and flow channel device 50 according to the first embodiment will be simplified or omitted, and different points will mainly be described.

The flow channel device 150 includes an electrical guard portion 80 (second guard portion) provided in the measurement portion 20. The guard portion 80 includes a guard electrode pair 86 and 87 intersecting the measurement electrodes 21 and 22 of the measurement portion 20. Specifically, the measurement electrode 21 and the guard electrode 86 are provided while the resin film 5 is interposed therebetween, and the measurement electrode 22 and the guard electrode 87 are provided while the resin film 5 is interposed therebetween.

In this embodiment, since the measurement electrode 22 and the guard electrode 86 are a common electrode, a surface area of the common electrode of the measurement portion 20 according to the second embodiment is almost twice the surface area of the measurement electrode 22 according to the first embodiment.

Further, the flow channel device 150 includes the guard portion 30 (first guard portion) between the measurement portion 20 and the operation portion 40 as in the first embodiment.

As described above, by providing the guard portion 80 closer to the measurement electrodes 21 and 22 than the guard portion 30, noises in measurement values obtained by the measurement portion 20 can be additionally reduced, and measurement accuracy can be improved.

In this embodiment, the guard electrode 36 on the upper side of the guard portion 30 and the guard electrode 86 of the guard portion 80 on the right-hand side of the figure may be constituted of a single electrode.

(Outer Appearance of Flow Channel Device)

Figure 10:
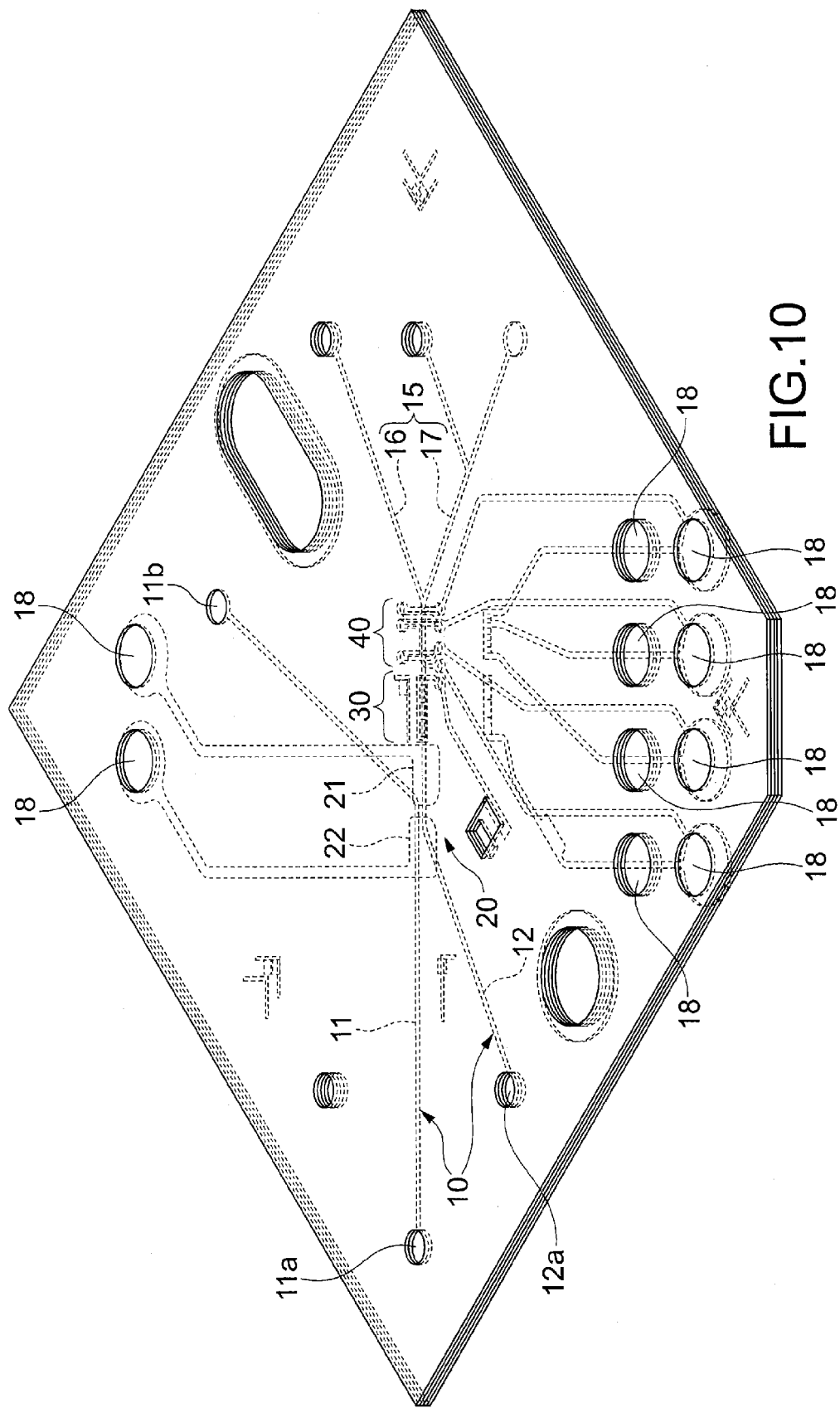
FIG. 10 is a perspective view showing a more-specific example of the flow channel device.

FIG. 10 is a perspective view showing a more-specific example of the flow channel device. In the figure, the lateral direction corresponds to the x direction. The first flow channel 11, the second flow channel 12, the branch portion 15, the measurement portion 20, the guard portion 30, the operation portion 40, an electrode pad 18, and the like are provided. The first flow channel 11 and the second flow channel 12 are provided while intersecting each other near the measurement portion 20 instead of being parallel and are mutually connected by a narrowed channel (not shown). The drainage outlet 11b of the first flow channel 11 is also provided.

It should be noted that in the flow channel device, the electrode of the operation portion 40 is divided into a plurality of parts along the flow channel 10 as will be described later, and the number of electrode pads 18 is increased that much.

[Other Embodiments]

The present disclosure is not limited to the embodiments described above, and various other embodiments can also be realized.

The guard electrodes 36 and 37 are provided while opposing each other on the upper portion side and lower portion side of the flow channel, but a single electrode may be provided on one of the upper portion side and the lower portion side. Alternatively, the guard electrodes 36 and 37 may be provided on at least one of the side walls in addition to the upper portion side and the lower portion side.

The shape of the guard electrodes 36 and 37 is rectangular as shown in FIG. 3, but the guard electrodes 36 and 37 may be a circle, an oval, a shape obtained by combining a circle and a rectangle, or other arbitrary shapes.

The shape of the line electrodes 42a and 42b of the guide electrode portion 42 is not limited to the shape shown in FIG. 3, and the line electrodes 42a and 42b may take other shapes. For example, the line electrode may be divided into a plurality of parts along the flow of the flow channel. Alternatively, the straight portion and the direction change portion may be separated.

A hole or a slit may be provided in the guard electrodes 36 and 37. With this structure, the inside of the flow channel 10 can be observed by an observer from outside the flow channel device via the hole or slit using a microscope or the like.

The voltage to be applied to the operation electrode 410 may be a DC voltage instead of the AC voltage.

Of the feature portions of the embodiments described above, at least two of the feature portions can be combined.

The present disclosure may also take the following structures.

(1) A flow channel device, including:
a flow channel through which a fluid including particles flow;
a plurality of branch channels branching from the flow channel;
a measurement portion that is provided at a predetermined position in the flow channel and configured to measure electrical characteristics when the particles pass the predetermined position;
an operation portion that is provided on a downstream side of the measurement portion and on an upstream side of the plurality of branch channels and configured to apply a dielectrophoretic force to the particles by forming an electric field; and
an electrical first guard portion provided between the measurement portion and the operation portion.

(2) The flow channel device according to (1),
in which the first guard portion includes a guard electrode facing an inside of the flow channel.

(3) The flow channel device according to (2),
in which the guard electrode is provided on at least one of two opposing sides of the flow channel.

(4) The flow channel device according to (2) or (3),
in which the guard electrode includes a common potential.

(5) The flow channel device according to any one of (2) to (4), further including
an electrical second guard portion provided in the measurement portion.

(6) The flow channel device according to (5),
in which the measurement portion includes a measurement electrode pair, and
in which the second guard portion includes a guard electrode pair intersecting the measurement electrode pair.

(7) The flow channel device according to any one of (2) to (6),
in which the flow channel device is structured by laminating a plurality of resin films, and
in which the guard electrode is formed of at least one of the plurality of resin films.

(8) The flow channel device according to (7),
in which at least two of the plurality of resin films are formed of the same material, and
in which the guard electrode is a guard electrode pair opposing the two resin films.

(9) A sorting apparatus, including:
a flow channel device including
a flow channel through which a fluid including particles flow,
a plurality of branch channels branching from the flow channel,
a measurement portion that is provided at a predetermined position in the flow channel and measures electrical characteristics when the particles pass the predetermined position,
an operation portion that is provided on a downstream side of the measurement portion and on an upstream side of the plurality of branch channels and applies a dielectrophoretic force to the particles by forming an electric field, and
an electrical first guard portion provided between the measurement portion and the operation portion; and
a controller that is electrically connected to the measurement portion and the operation portion and configured to generate an operation signal based on a signal obtained by the measurement portion and output the operation signal.

It should be understood by those skilled in the art that various modifications, combinations, sub-combinations and alterations may occur depending on design requirements and other factors insofar as they are within the scope of the appended claims or the equivalents thereof.

What is claimed is:

1. A flow channel device, comprising:
a flow channel through which a fluid including particles flows;
a plurality of branch channels branching from the flow channel;
a measurement portion, including a first measurement electrode and a second measurement electrode, that is provided at a predetermined position in the flow channel and configured to measure electrical characteristics in an event of the particles pass the predetermined position;
an operation portion that is provided on a downstream side of the measurement portion and on an upstream side of the plurality of branch channels and configured to apply a dielectrophoretic force to the particles by forming an electric field;
an electrical first guard portion provided between the measurement portion and the operation portion; and
an electrical second guard portion, including a first guard electrode and a second guard electrode, on upstream side of the electrical first guard portion,
wherein the first guard electrode and the first measurement electrode are on a first side of a resin film of the flow channel, and the second guard electrode and the second measurement electrode are on a second side opposite to the first side of the resin film.

2. The flow channel device according to claim 1,
wherein the electrical first guard portion includes a guard electrode facing an inside of the flow channel.

3. The flow channel device according to claim 2,
wherein the guard electrode is provided on at least one of two opposing sides of the flow channel.

4. The flow channel device according to claim 2,
wherein the guard electrode includes a common potential.

5. The flow channel device according to claim 2, wherein the electrical second guard portion provided in the measurement portion.

6. The flow channel device according to claim 5,
wherein the second guard portion includes a guard electrode pair intersecting a measurement electrode pair,
wherein the guard electrode pair includes the first guard electrode and the second guard electrode, and
wherein the measurement electrode pair includes the first measurement electrode and the second measurement electrode.

7. The flow channel device according to claim 2,
wherein the flow channel device is structured by laminating a plurality of resin films, and
wherein the guard electrode is formed of at least one of the plurality of resin films.

8. The flow channel device according to claim 7,
wherein at least two of the plurality of resin films are formed of the same material, and
wherein the guard electrode is a guard electrode pair opposing the at least two of the plurality of resin films.

9. A sorting apparatus, comprising:
a flow channel device including
   a flow channel through which a fluid including particles flows,
   a plurality of branch channels branching from the flow channel,
   a measurement portion, including a first measurement electrode and a second measurement electrode, that is provided at a predetermined position in the flow channel and configured to measure electrical characteristics in an event of the particles pass the predetermined position,
   an operation portion that is provided on a downstream side of the measurement portion and on an upstream side of the plurality of branch channels and configured to apply a dielectrophoretic force to the particles by forming an electric field,
   an electrical first guard portion provided between the measurement portion and the operation portion, and
   an electrical second guard portion, including a first guard electrode and a second guard electrode, on upstream side of the electrical first guard portion,
      wherein the first guard electrode and the first measurement electrode are on a first side of a resin film of the flow channel, and the second guard electrode and the second measurement electrode are on a second side opposite to the first side of the resin film; and
a controller that is electrically connected to the measurement portion and the operation portion and configured to generate an operation signal based on a signal obtained by the measurement portion and output the operation signal.

* * * * *